(12) United States Patent
Chandra et al.

(10) Patent No.: US 8,311,182 B2
(45) Date of Patent: Nov. 13, 2012

(54) SYSTEM AND METHOD OF NOTCH FILTRATION FOR DUAL ENERGY CT

(75) Inventors: Naveen Chandra, Kenosha, WI (US); Bruno Kristiaan Bernard De Man, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 56 days.

(21) Appl. No.: 12/887,584

(22) Filed: Sep. 22, 2010

(65) Prior Publication Data
US 2012/0069953 A1   Mar. 22, 2012

(51) Int. Cl.
*A61B 6/00* (2006.01)
*G06K 9/00* (2006.01)

(52) U.S. Cl. ........ 378/5; 378/98.9; 378/98.12; 382/130; 382/131

(58) Field of Classification Search ............... 378/4, 5, 378/98.9, 98.12; 382/130
See application file for complete search history.

(56) References Cited

U.S. PATENT DOCUMENTS

| | | | | |
|---|---|---|---|---|
| 3,974,386 A * | 8/1976 | Mistretta et al. | ........... | 378/98.11 |
| 4,355,331 A * | 10/1982 | Georges et al. | ........... | 378/98.11 |
| 4,399,550 A * | 8/1983 | Hauck et al. | ........... | 378/5 |
| 4,482,918 A * | 11/1984 | Keyes et al. | ........... | 378/98.11 |
| 4,578,803 A * | 3/1986 | Macovski | ........... | 378/62 |
| 4,686,695 A * | 8/1987 | Macovski | ........... | 378/146 |
| 4,887,604 A * | 12/1989 | Shefer et al. | ........... | 600/431 |
| 5,020,085 A * | 5/1991 | Kawara et al. | ........... | 378/98.11 |
| 5,285,489 A | 2/1994 | Ohtsuchi et al. | | |
| 5,365,567 A | 11/1994 | Ohtsuchi et al. | | |
| 6,246,747 B1 * | 6/2001 | Wear et al. | ........... | 378/98.9 |
| 6,836,535 B2 * | 12/2004 | Toth et al. | ........... | 378/159 |
| 7,636,413 B2 | 12/2009 | Toth | | |
| 7,688,935 B2 * | 3/2010 | Toth | ........... | 378/5 |
| 7,688,936 B2 | 3/2010 | Toth | | |
| 2002/0196899 A1 * | 12/2002 | Karellas | ........... | 378/98.8 |
| 2005/0226376 A1 * | 10/2005 | Yun et al. | ........... | 378/62 |
| 2007/0237288 A1 * | 10/2007 | Tkaczyk et al. | ........... | 378/5 |
| 2008/0069298 A1 * | 3/2008 | Hoffman et al. | ........... | 378/19 |
| 2008/0232549 A1 * | 9/2008 | Poorter | ........... | 378/98.9 |
| 2009/0135994 A1 * | 5/2009 | Yu et al. | ........... | 378/5 |

* cited by examiner

*Primary Examiner* — Alexander H Taningco
(74) *Attorney, Agent, or Firm* — Ziolkowski Patent Solutions Group, SC

(57) ABSTRACT

An imaging system includes an x-ray source that emits a beam of x-rays toward an object to be imaged, a detector that receives the x-rays attenuated by the object, a spectral notch filter positioned between the x-ray source and the object, a data acquisition system (DAS) operably connected to the detector, and a computer operably connected to the DAS and programmed to acquire a first image dataset at a first kVp, acquire a second image dataset at a second kVp that is greater than the first kVp, and generate an image of the object using the first image dataset and the second image dataset.

22 Claims, 7 Drawing Sheets

US 8,311,182 B2

SYSTEM AND METHOD OF NOTCH FILTRATION FOR DUAL ENERGY CT

BACKGROUND

The present invention relates generally to diagnostic imaging and, more particularly, to a system and method of basis material decomposition having an increased separation of mean energies between low and high kVp projections.

Medical imaging devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction. Such typical systems, however, do not include an ability to discriminate spectral energy content of x-rays as they pass through an object being imaged.

However, as known in the art, dual or multi-energy spectral CT systems have been developed that can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged and the relative composition of an object composed of two hypothetical materials.

Different approaches have been developed to realize dual energy or spectral imaging. To name a few, dual x-ray source and detector, a single x-ray source with an energy discriminative detector, and a single x-ray source and detector with multiple acquisitions at different kVp or interleaved with fast kVp switching capability are examples of techniques.

In a dual x-ray source and detector system, typically two x-ray sources are provided, each having a respective detector positioned opposite thereto such that x-rays may be emitted from each source having a different spectral energy content. Thus, based on the known energy difference of the sources, a scintillating or energy integrating device may suffice to distinguish energy content and different materials within the object being imaged.

In a single x-ray source with an energy discriminative detector, energy sensitive detectors may be used such that each x-ray photon reaching the detector is recorded with its photon energy. Such systems may use a direct conversion detector material in lieu of a scintillator.

In a single x-ray source and detector arrangement, a conventional third generation CT system may acquire projections sequentially at different peak kilovoltage (kVp) levels, which changes the peak and spectrum of energy of the incident photons comprising the emitted x-ray beams. Two scans are acquired—either (1) back-to-back sequentially in time where the scans require two rotations around the subject, or (2) interleaved as a function of the rotation angle requiring one rotation around the subject, in which the tube operates at, for instance, 80 kVp and 140 kVp potentials.

When dual energy data is acquired back-to-back, imaging data acquired during subsequent source/detector gantry rotations is prone to motion artifacts because of the motion that occurs during each subsequent rotation. When interleaved, in contrast, an input voltage to the x-ray source is switched quickly between the low and high kVp potentials, which allows a close correlation between imaging data sets. However, because the switching occurs very rapidly on a single x-ray source, there is little opportunity to change the filtration between the two samples. As a result, there is a spectral (energy) overlap between the two samples that inherently limits the amount of energy separation between them. As known in the art, it is desirable to increase energy separation between low and high kVp operation in order to increase the contrast-to-noise ratio. However, it is not feasible to simply decrease the low kVp or increase the high kVp in order to increase energy separation therebetween. Lowering the low kVp may have limited signal-to-noise and cause other limitations in image reconstruction. Increasing the high kVp may cause system instability and spit activity and may cause other limitations in system operation.

Therefore, it would be desirable to have a system and method of increasing energy separation in dual energy CT.

BRIEF DESCRIPTION

The present invention is directed to a system and method for providing increased energy separation in dual energy CT.

According to an aspect of the present invention, an imaging system includes an x-ray source that emits a beam of x-rays toward an object to be imaged, a detector that receives the x-rays attenuated by the object, a spectral notch filter positioned between the x-ray source and the object, a data acquisition system (DAS) operably connected to the detector, and a computer operably connected to the DAS and programmed to acquire a first image dataset at a first kVp, acquire a second image dataset at a second kVp that is greater than the first kVp, and generate an image of the object using the first image dataset and the second image dataset.

According to another aspect of the present invention, a method of dual energy CT imaging includes selecting a low kVp potential and a high kVp potential for dual energy imaging, selecting a k-edge filter based on the low kVp potential and the high kVp potential and based on a k-edge of a material in the k-edge filter, positioning the k-edge filter between a source and an object to be imaged, and acquiring imaging data with the source energized to the first kVp potential and with the source energized to the second kVp potential.

According to yet another aspect of the present invention, a method of dual energy CT imaging includes passing low kVp x-rays through a k-edge notch filter to generate a first x-ray spectrum, acquiring a first set of imaging data of an object using the first x-ray spectrum, passing high kVp x-rays through the k-edge notch filter to generate a second x-ray spectrum, acquiring a second set of imaging data of the object using the second x-ray spectrum, and generating an image using the first set of imaging data and the second set of imaging data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

Imaging devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. It will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
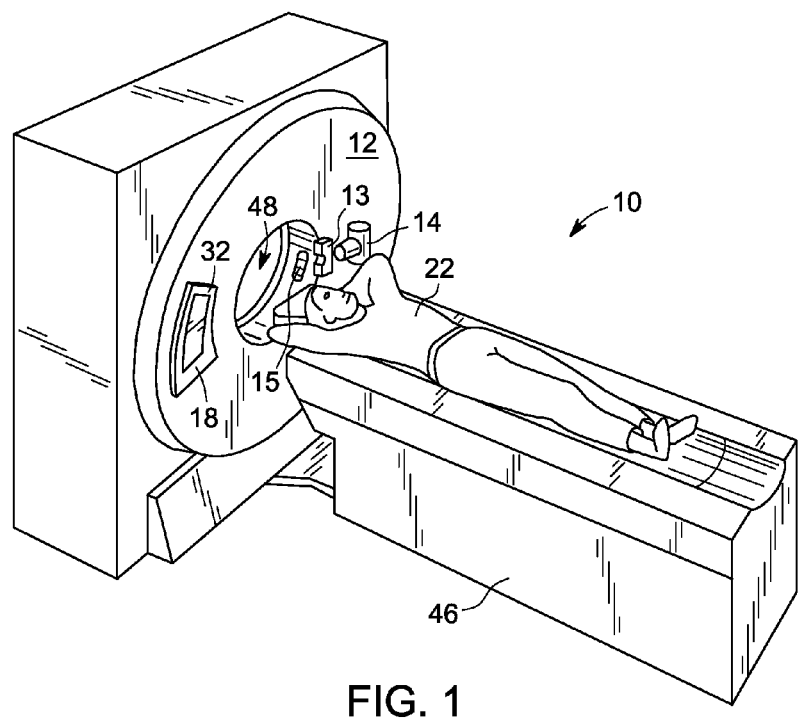
FIG. 1 is a pictorial view of a CT imaging system.
Figure 2:
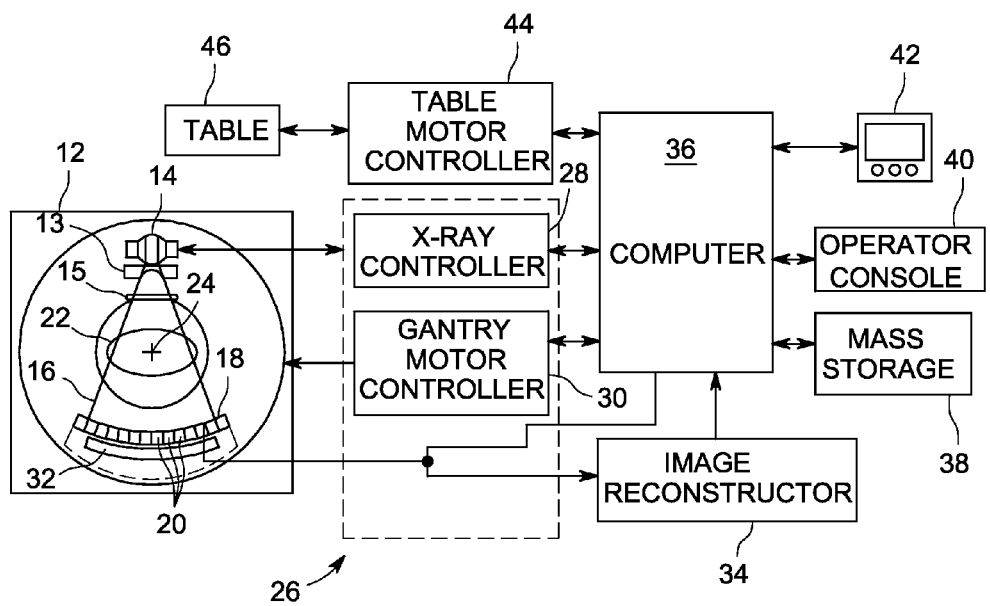
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 through a bowtie filter 13 and toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
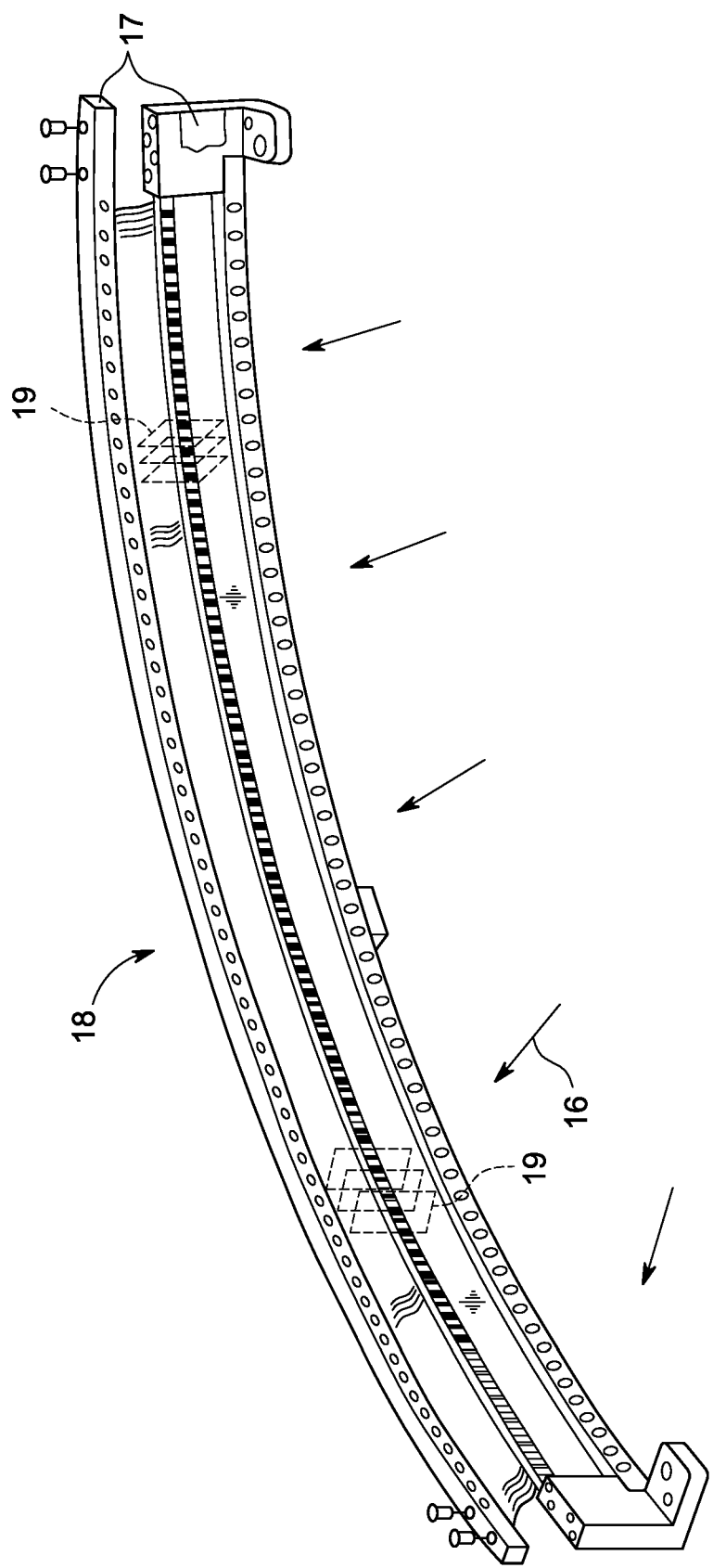
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
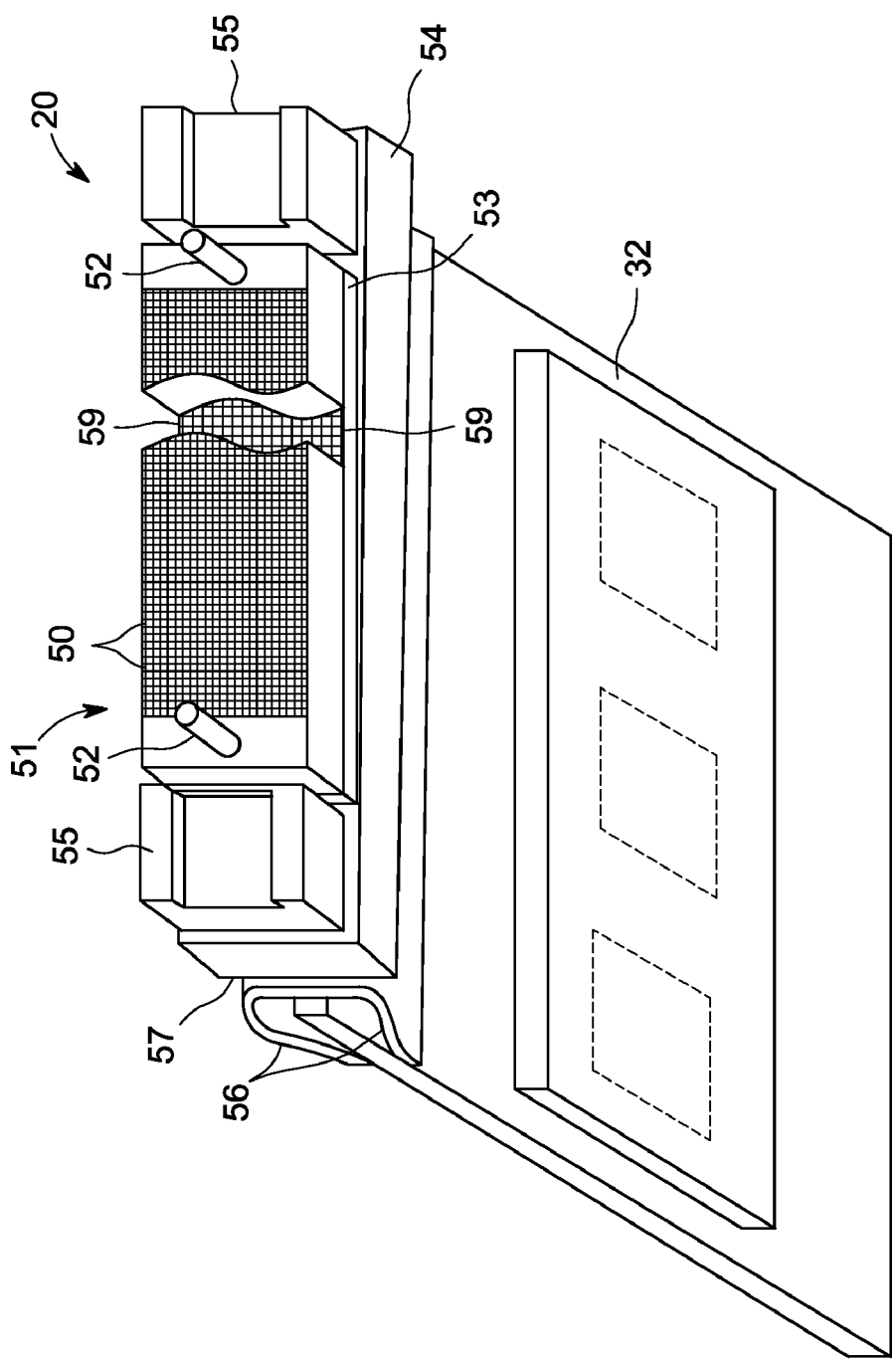
FIG. 4 is a perspective view of one embodiment of a CT detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Referring back to FIGS. 1 and 2, a discussion is now presented in connection with a decomposition algorithm. An image or slice is computed which may incorporate, in certain modes, less or more than 360 degrees of projection data to formulate an image. The image may be collimated to desired dimensions using tungsten blades in front of the x-ray source and different detector apertures. A collimator typically defines the size and shape of the beam of x-rays 16 that emerges from the x-ray source 14, and a bowtie filter 13 may be included in the system 10 to further control the dose to the patient 22. A typical bowtie filter attenuates the beam of x-rays 16 to accommodate the body part being imaged, such as head or torso, such that, in general, less attenuation is provided for x-rays passing through or near an isocenter of the patient 22. The bowtie filter shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps (such as water and iodine). The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known to have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, a compound or mixture of materials measured with a multiple energy technique may be represented as a hypothetical material (or combination of materials) having the same x-ray energy attenuation characteristics. This hypothetical material can be assigned an effective atomic number Z. Unlike the atomic number of an element, effective atomic number of a compound is defined by the x-ray attenuation characteristics, and it need not be an integer. This effective Z representation property stems from a well-known fact that x-ray attenuation in the energy range useful for diagnostic x-ray imaging is strongly related to the electron density of compounds, which is also related to the atomic number of materials.

Thus, dual-energy CT with fast kVp switching is an attractive way of achieving near simultaneous and near co-registered projection samples of two energies. However, because of the fast switching, there is little opportunity to change filtration between samples or otherwise increase energy separation between the low and high kVp energies. Thus, according to an embodiment of the invention, a single filter with an energy notch or k-edge in an overlapped region of the low and high kVp energies may be employed to increase energy separation therebetween.

Figure 5:
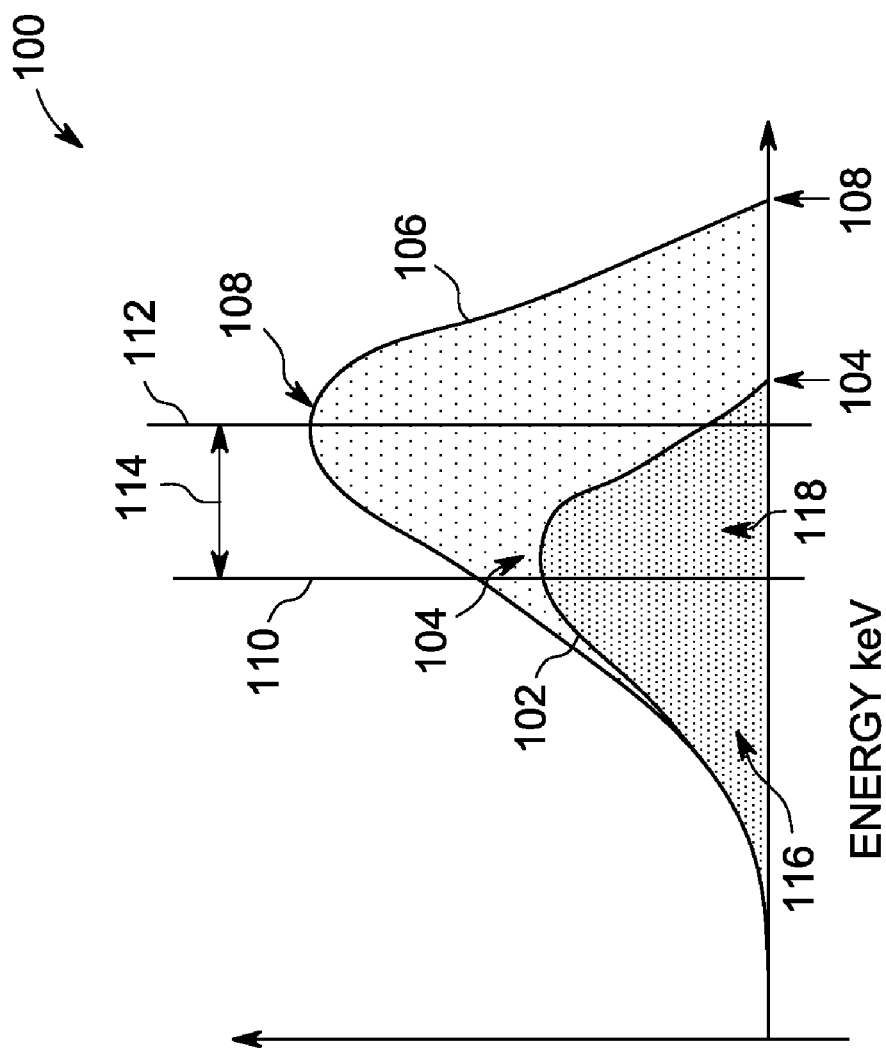
FIG. 5 is an illustration of energy spectra that includes a low energy spectrum and a high energy spectrum.

Referring to FIG. 5, an illustration 100 of energy spectra includes a low energy spectrum 102 having a first peak energy 104 and a high energy spectrum 106 having a second peak energy 108. Low energy spectrum 102 includes a first mean keV 110 and high energy spectrum 106 includes a second mean keV 112. An amount of energy separation 114 is illustrated between first mean keV 110 and second mean keV 112. As known in the art, each mean keV 110, 112 represents an energy or keV that approximately splits an amount of integrated area for each respective spectrum. Thus, for low energy spectrum 102, first mean keV 110 represents an energy level where an integrated energy below mean 116 is approximately equal to an integrated energy 118 above mean 116. Similarly, high energy spectrum 106 includes integrated energies (not marked) below and above second mean keV 112.

Spectra 102, 106 represent energy spectra emitted from an x-ray tube at respective peak energies 104, 108. In one example, a typical representation of respective energies is for equivalent patient filtration for an amount of water thickness. Thus, in this example that includes an equivalent patient filtration of 20 cm water, for a peak low kVp of 80 keV and for a peak high kVp of 140 keV, mean energies are approximately 55 keV and 76 keV, respectively. This results in an approximate energy separation of 21 keV (76 keV minus 55 keV) between low and high spectra.

However, when placing a k-edge material between an x-ray source and detector according to the invention, it is possible to increase energy separation between mean low kVp and mean high kVp. A k-edge indicates a sudden increase in the attenuation coefficient of photons occurring at a photon energy just above the binding energy of the K shell electron of the atoms interacting with the photons. The sudden increase in attenuation is due to photoelectric absorption of the photons. For this interaction to occur, the photons have more energy than the binding energy of the K shell electrons. A photon having an energy just above the binding energy of the electron is therefore more likely to be absorbed than a photon having an energy just below this binding energy. A general term for the phenomenon is absorption edge.

Because of this sudden jump in attenuation, it is possible to increase separation of mean energies of low and high kVp spectra, according to the invention. In one example, for 20 cm of water and 0.5 mm Hf (k-edge of approximately 65.4 keV), mean energies of low and high are respectively, approximately 58 keV and 86 keV, resulting in a separation of approximately 28 keV—which is an increase from 21 keV as illustrated above. Referring back to FIGS. 1 and 2, k-edge material 15 may be positioned between x-ray source 14 and detector assembly 18, and more particularly between x-ray source 14 and patient 22. As such, with placement of an attenuating material having a k-edge that falls between mean energies of the low kVp and high kVp spectra it is possible to increase separation therebetween, according to the invention.

Thus, in general and according to the invention, it is possible to increase energy separation between low and high kVp spectra by selecting a k-edge notch filter having a k-edge that falls between the mean energies of the low and high kVp spectra. Typically, such a filter may have a thickness of approximately 1 mm. However, it is to be understood that the thickness is dependent on specific desired imaging characteristics including but not limited to low and high kVp spectra, mA, patient characteristics, anatomy, and the like.

In an example, low and high kVp spectra are respectively 80 keV and 140 keV. And, in one example the low kVp potential and the high kVp potential are each for a period less than one millisecond. However, it is to be understood that any low and high kVp spectra may be selected for dual or multi-energy imaging, according to the invention. It is also to be understood that one millisecond duration at low and high kVp potentials is an example, and that any length period may be implemented, depending on imaging application, according to the invention. Further, although Hf is given above as an example k-edge material, according to the invention any material having a k-edge between mean low kVp 110 and mean high kVp 112 may suffice. Thus, for dual energy imaging, typical desired k-edge materials may range between approximately 30 keV and 80 keV.

Figure 6:
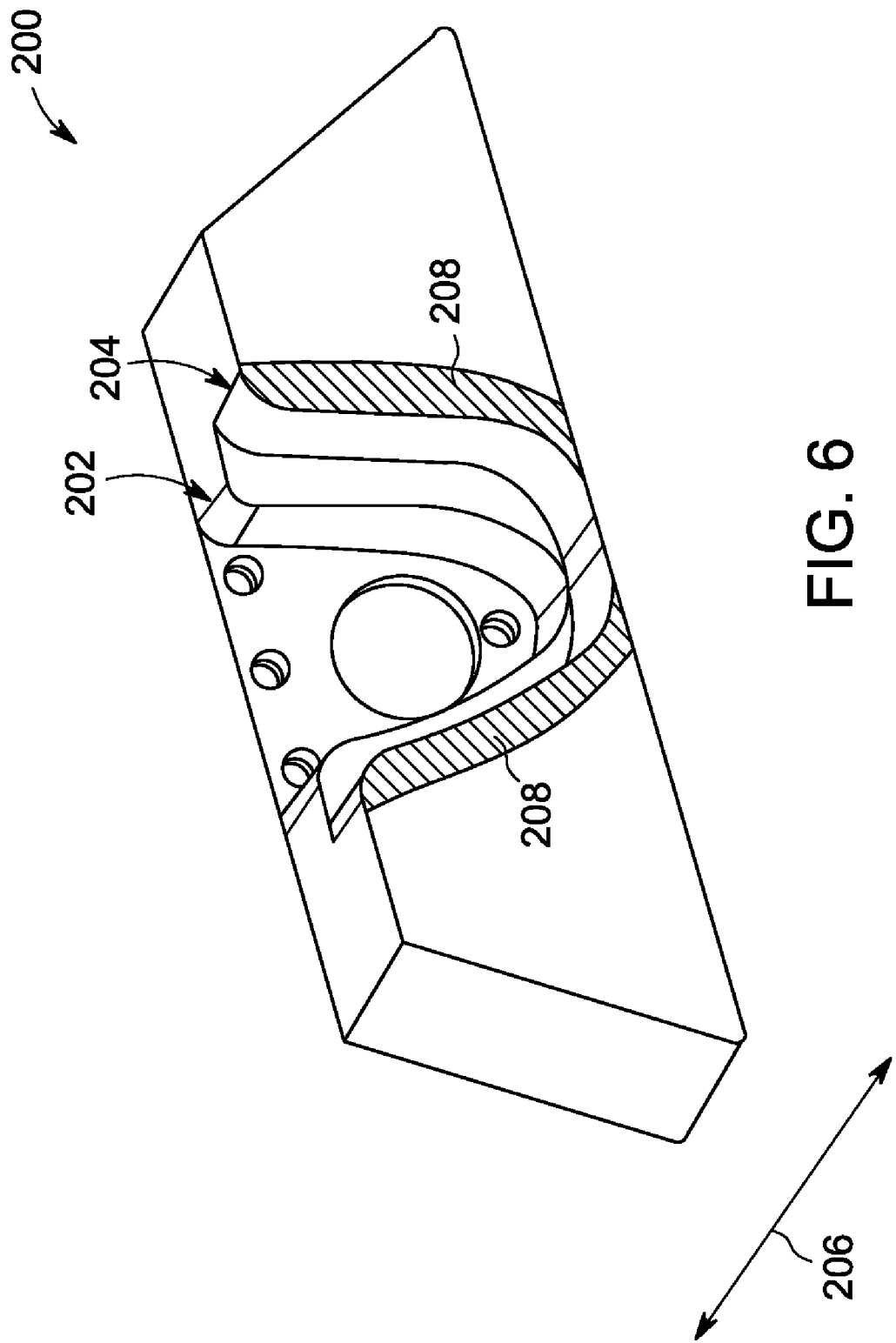
FIG. 6 is an illustration of a bowtie filter with k-edge material according to an embodiment of the invention.

Although bowtie filter 13 and k-edge filter 15 are illustrated as separate elements FIGS. 1 and 2, it is possible to combine both into a single apparatus that includes both bowtie filtration and k-edge filtration. Referring now to FIG. 6, a bowtie filter is illustrated according to an embodiment of the invention. Typically, a bowtie filter may include multiple bowties that may be accessed by selectively placing the bowtie filter at a preferred axial location. FIG. 6 is an illustration of one example of a bowtie filter unit 200 having two sizes of bowtie 202, 204 therein. Each bowtie 202, 204 is positioned along an axis 206 of bowtie filter unit 200. Thus, when in operation, bowtie filter unit 200 may be selectively placed axially, based on an anatomy that is to be imaged, or based on a patient that is to be imaged. As such, in one example for a relatively small body, bowtie filter 202 may be selected, while for a relatively large body, bowtie filter 204 may be selected. And, bowtie filter unit 200 may not be limited to two sizes of bowtie 202, 204, but may include many bowties that are positionable along axis 206. Bowtie filter 200 may include a k-edge material that can serve a dual purpose of providing bowtie beam shaping as well as k-edge filtration. Thus, bowtie filter 200 may include a k-edge material in one or both bowties 202, 204, as illustrated in phantom as an example as k-edge material 208.

Figure 7:
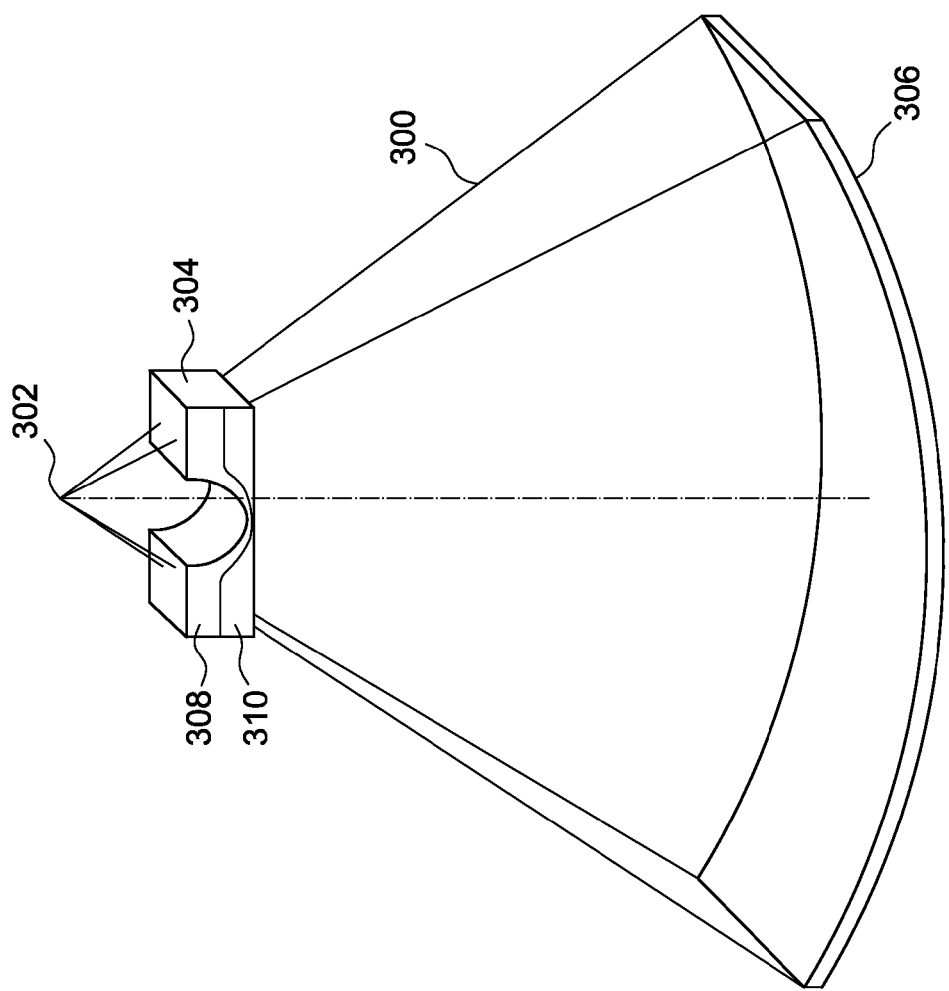
FIG. 7 is an illustration of a multi-material k-edge filter, according to embodiments of the invention.

It is possible to enhance filtration, selectability, separation of spectra, and more controlled shaping of the energy spectrum by combining two or more k-edge filters. Thus, according to embodiments of the invention, two or more k-edge materials may be included in a k-edge filter. FIG. 7 is thus an illustration of a multi-material k-edge filter, according to an embodiment of the invention. FIG. 7 is an illustration of x-rays 300 that emanate from a focal spot or point 302, which may be for instance a focal spot or point within an x-ray source such as x-ray tube 14 of FIGS. 1 and 2. X-rays 300 pass through a multi-material k-edge filter 304, through a patient or object (not shown), and toward a detector array or assembly 306 (which may be, in an example, detector assembly 18 of FIGS. 1 and 2).

As illustrated, multi-material k-edge filter 304 includes a first material 308 and a second material 310. In embodiments of the invention, first and second materials 308, 310 are k-edge materials that, in combination, enable a selective and controlled shaping of the energy spectrum, which can lead to distinct notch filtration when compared to a single k-edge material. As such, a combination of k-edge materials may be selected in order to specifically affect a level of filtration at a specific energy, while leaving portions of the spectrum outside this specifically affected area intact. And, although two materials 308, 310 are illustrated, it is to be understood that more than two materials may be included, limited only by a combined and desired total attenuation and space available for placement of multi-material k-edge filter 304. It is to be understood that the use of multi-material k-edge filter 304 may be in combination with a separate conventional bowtie filter, or multi-material k-edge filter 304 may be combined with a bowtie filter to provide both k-edge filtration and bowtie beam shaping in a single unit. As stated above with respect to a single k-edge material filter, combinations of materials may be selected, each having for instance a k-edge that falls between approximately 30 keV and 80 keV.

In one example, Hf (hafnium) and W (tungsten) may be combined to enable an improved optimization over Hf alone. This combination of k-edge materials allows selective choice of a region of the spectrum that is desired to be affected to tune attenuation in that region of the spectrum. Further, Hf and W are used as an example of a combination of materials. However, depending on the energy range that is desired to be affected, different materials can be selected based on their k-edge, density, and the like, which can be combined to create the effect at selected energy ranges in the spectrum.

Figure 8:
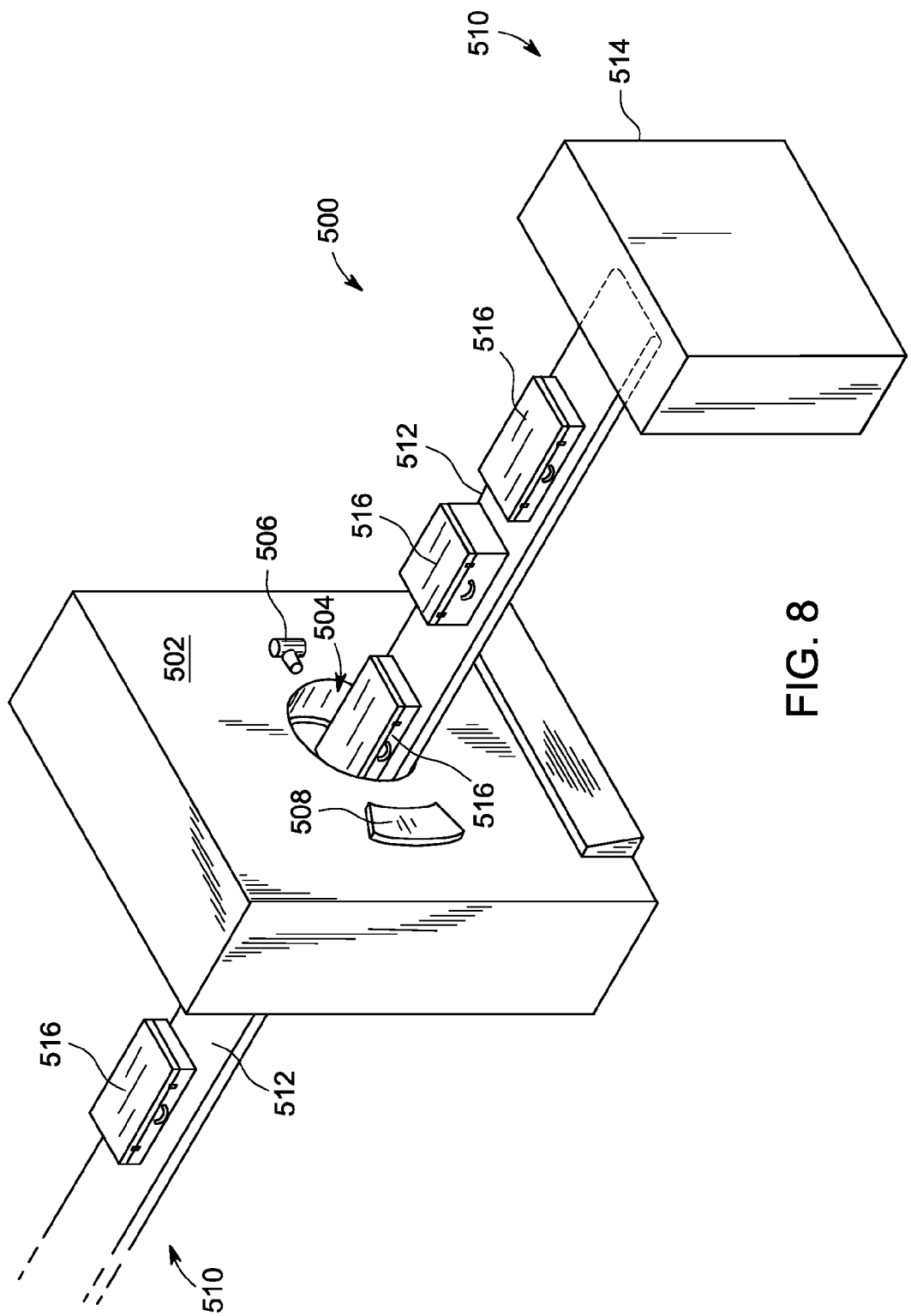
FIG. 8 is a pictorial view of a CT system for use with a non-invasive package inspection system.

Referring now to FIG. 8, package/baggage inspection system 500 includes a rotatable gantry 502 having an opening 504 therein through which packages or pieces of baggage may pass. The rotatable gantry 502 houses an x-ray and/or high frequency electromagnetic energy source 506 as well as a detector assembly 508 having scintillator arrays comprised of scintillator cells. A conveyor system 510 is also provided and includes a conveyor belt 512 supported by structure 514 to automatically and continuously pass packages or baggage pieces 516 through opening 504 to be scanned. Objects 516 are fed through opening 504 by conveyor belt 512, imaging data is then acquired, and the conveyor belt 512 removes the packages 516 from opening 504 in a controlled and continuous manner. As a result, postal inspectors, baggage handlers, and other security personnel may non-invasively inspect the contents of packages 516 for explosives, knives, guns, contraband, etc. An exemplary implementation can aid in the development of automatic inspection techniques, such as explosive detection in luggage.

A technical contribution for the disclosed method and apparatus is that is provides for a computer implemented system and method of basis material decomposition having an increased separation of mean energies between low and high kVp projections.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, according to an embodiment of the invention, an imaging system includes an x-ray source that emits a beam of x-rays toward an object to be imaged, a detector that receives the x-rays attenuated by the object, a spectral notch filter positioned between the x-ray source and the object, a data acquisition system (DAS) operably connected to the detector, and a computer operably connected to the DAS and programmed to acquire a first image dataset at a first kVp, acquire a second image dataset at a second kVp that is greater than the first kVp, and generate an image of the object using the first image dataset and the second image dataset.

According to another embodiment of the invention, a method of dual energy CT imaging includes selecting a low kVp potential and a high kVp potential for dual energy imaging, selecting a k-edge filter based on the low kVp potential and the high kVp potential and based on a k-edge of a material in the k-edge filter, positioning the k-edge filter between a source and an object to be imaged, and acquiring imaging data with the source energized to the first kVp potential and with the source energized to the second kVp potential.

According to yet another embodiment of the invention, a method of dual energy CT imaging includes passing low kVp x-rays through a k-edge notch filter to generate a first x-ray spectrum, acquiring a first set of imaging data of an object using the first x-ray spectrum, passing high kVp x-rays through the k-edge notch filter to generate a second x-ray spectrum, acquiring a second set of imaging data of the object using the second x-ray spectrum, and generating an image using the first set of imaging data and the second set of imaging data.

The present invention has been described in terms of the preferred embodiment, and it is recognized that equivalents, alternatives, and modifications, aside from those expressly stated, are possible and within the scope of the appending claims.

What is claimed is:

1. An imaging system comprising:
   an x-ray source that emits a beam of x-rays toward an object to be imaged;
   a detector that receives the x-rays attenuated by the object;
   a spectral notch filter positioned between the x-ray source and the object;
   a data acquisition system (DAS) operably connected to the detector; and
   a computer operably connected to the DAS and programmed to:
   acquire a first image dataset at a first kVp;
   acquire a second image dataset at a second kVp that is greater than the first kVp; and
   generate an image of the object using the first image dataset and the second image dataset.

2. The imaging system of claim 1 wherein the first kVp includes a mean kVp that is less than a k-edge of the notch filter, and wherein the second kVp includes a mean kVp that is greater than the k-edge of the notch filter.

3. The imaging system of claim 1 comprising a bowtie filter positioned between the x-ray source and the object, wherein the bowtie filter includes the spectral notch filter.

4. The imaging system of claim 3 wherein the bowtie filter includes a first bowtie at a first axial location and a second bowtie at a second axial location, and wherein the spectral notch filter is positioned in the bowtie at the first axial location.

5. The imaging system of claim 1 wherein the first kVp is approximately 80 kVp and the second kVp is approximately 140 kVp.

6. The imaging system of claim 1 wherein the computer is programmed to decompose the first image dataset and the second image dataset into a first basis material image and a second basis material image, wherein the first basis material image is one of an iodine image and a water image.

7. The imaging system of claim 1 wherein the computer is further programmed to:
   cause the x-ray source to emit a first beam of x-rays at the first kVp;
   cause the x-ray source to emit a second beam of x-rays at the second kVp;
   acquire the first image dataset using the first beam of x-rays; and
   acquire the second image dataset using the second beam of x-rays.

8. The imaging system of claim 1 wherein the spectral notch filter includes a first k-edge material having a first k-edge and a second k-edge material having a second k-edge, wherein the x-rays attenuated by the object pass through both the first k-edge material and the second k-edge material.

9. The imaging system of claim 1 wherein the spectral notch filter includes a first k-edge material having a first k-edge and is positioned between the x-ray source and the object during the acquisition of the first image dataset at the first kVp and during the acquisition of the second image dataset at the second kVp.

10. The imaging system of claim 1 wherein the computer is programmed to generate the image by being programmed to convert measured projections of the first image dataset and of the second image dataset to density line-integral projections, form density maps of basis materials based on the density line-integral projections, and form a volume rendering of one of the basis materials based on the density maps.

11. A method of dual energy CT imaging comprising:
selecting a low kVp potential and a high kVp potential for dual energy imaging;
selecting a k-edge filter based on the low kVp potential and the high kVp potential and based on a k-edge of a material in the k-edge filter;
positioning the k-edge filter between a source and an object to be imaged; and
acquiring imaging data with the source energized to the first kVp potential and with the source energized to the second kVp potential.

12. The method of claim 11 wherein the step of selecting the k-edge filter comprises selecting the k-edge filter such the k-edge of the material in the filter is above a peak kVp of the low kVp potential and below a peak kVp of the high kVp potential.

13. The method of claim 11 comprising positioning a bowtie filter between the source and the object to be imaged, wherein the bowtie filter includes the selected k-edge filter.

14. The method of claim 11 comprising:
decomposing the imaging data into a first basis material image and a second basis material image; and
generating a final image based on the first basis material image and the second basis material image.

15. The method of claim 11 comprising:
selecting a bowtie filter having a first bowtie profile at a first axial location and a second bowtie profile at a second axial location;
wherein the selected k-edge filter is within the bowtie filter at one of the first axial locations and the second axial locations.

16. The method of claim 11 wherein the k-edge filter comprises a first k-edge material and a second k-edge material, such that the imaging data acquired with the source energized to the first kVp is acquired from x-rays having passed through both the first k-edge material and the second k-edge material.

17. The method of claim 11 wherein the step of acquiring the imaging data comprises acquiring the imaging data while the k-edge filter is positioned between the source and the object to be imaged when the source is energized to the first kVp potential and when the source is energized to the second kVp potential.

18. A method of dual energy CT imaging comprising:
passing low kVp x-rays through a k-edge notch filter to generate a first x-ray spectrum;
acquiring a first set of imaging data of an object using the first x-ray spectrum;
passing high kVp x-rays through the k-edge notch filter to generate a second x-ray spectrum;
acquiring a second set of imaging data of the object using the second x-ray spectrum; and
generating an image using the first set of imaging data and the second set of imaging data.

19. The method of claim 18 comprising selecting the k-edge notch filter based on the low kVp and the high kVp.

20. The method of claim 18 comprising positioning a bowtie filter between the object and an x-ray source that is used to generate the low kVp x-rays and the high kVp x-rays, wherein the bowtie filter includes the k-edge notch filter.

21. The method of claim 20 wherein the bowtie filter includes a first bowtie profile, and a second bowtie profile that is axially offset from the first bowtie profile, wherein one of the first and second bowtie profiles includes the kedge notch filter.

22. The method of claim 18 wherein the step of generating the images comprises generating the image by converting measured projections of the first set of imaging data and of the second set of imaging data to density line-integral projections, forming density maps of basis materials based on the density line-integral projections, and forming a volume rendering of one of the basis materials based on the density maps.

* * * * *